United States Patent
Hong et al.

(10) Patent No.: US 10,528,531 B2
(45) Date of Patent: Jan. 7, 2020

(54) METHOD FOR VERIFYING BIODATA, AND APPARATUS THEREFOR

(71) Applicant: KT CORPORATION, Gyeonggi-do (KR)

(72) Inventors: Chang-Bum Hong, Seoul (KR); Mi-Sook Lee, Seoul (KR); Han-Kyu Choi, Seoul (KR); Dae-Chul Choi, Gyeonggi-do (KR)

(73) Assignee: KT CORPORATION, Gyeonggi-do (KR)

( * ) Notice: Subject to any disclaimer, the term of this patent is extended or adjusted under 35 U.S.C. 154(b) by 869 days.

(21) Appl. No.: 14/649,546

(22) PCT Filed: Jul. 18, 2013

(86) PCT No.: PCT/KR2013/006451
§ 371 (c)(1),
(2) Date: Jun. 3, 2015

(87) PCT Pub. No.: WO2014/088179
PCT Pub. Date: Jun. 12, 2014

(65) Prior Publication Data
US 2017/0147614 A1     May 25, 2017

(30) Foreign Application Priority Data

Dec. 3, 2012  (KR) ........................ 10-2012-0139109

(51) Int. Cl.
| | | |
|---|---|---|
| *G06F 16/215* | (2019.01) | |
| *G16B 50/00* | (2019.01) | |
| *G06F 11/08* | (2006.01) | |

(52) U.S. Cl.
CPC ............ *G06F 16/215* (2019.01); *G06F 11/08* (2013.01); *G16B 50/00* (2019.02)

(58) Field of Classification Search
None
See application file for complete search history.

(56) References Cited

U.S. PATENT DOCUMENTS

| | | |
|---|---|---|
| 2012/0029934 A1 | 2/2012 | Shindo et al. |
| 2012/0102041 A1 | 4/2012 | Park et al. |
| 2012/0135409 A1 | 5/2012 | Faham et al. |
| 2012/0173157 A1 | 7/2012 | Ahn et al. |

FOREIGN PATENT DOCUMENTS

| | | |
|---|---|---|
| JP | 2008-020312 A | 1/2008 |
| JP | 2011-247907 A | 12/2011 |
| JP | 2012-026947 A | 2/2012 |
| KR | 10-2003-0000452 A | 1/2003 |
| KR | 10-0696708 B1 | 3/2007 |
| KR | 10-2012-0079320 A | 7/2012 |
| KR | 10-1188886 B1 | 10/2012 |

*Primary Examiner* — Joseph Woitach
(74) *Attorney, Agent, or Firm* — IP Legal Services, LLC

(57) ABSTRACT

The present disclosure relates to a method and an apparatus for verifying biodata by verifying, in real-time, whether there are errors in biodata received from a client terminal. The method may include the steps of: receiving a request to upload biodata from the client terminal and storing the biodata to a storage system; extracting sequences from the biodata and verifying whether the sequences are valid data; upon detection of errors in a sequence, calculating an error ratio of the sequence and, when the calculated error ratio exceeds a threshold value, terminating the upload of the biodata.

10 Claims, 4 Drawing Sheets

FIG. 3

```
1st row - sequence ID starting with a character '@'
2nd row - sequencing information containing characters of 'A', 'T', 'G', 'C', and 'N'
3rd row - option information starting with '+'
4th row - quality score represented as ACSII code
```

METHOD FOR VERIFYING BIODATA, AND APPARATUS THEREFOR

CROSS REFERENCE TO RELATED APPLICATIONS

This application is a National Stage Patent Application of PCT International Patent Application No. PCT/KR2013/006451 (filed on Jul. 18, 2013) under 35 U.S.C. § 371, which claims priority to Korean Patent Application No. 10-2012-0139109 (filed on Dec. 3, 2012), the teachings of which are incorporated herein in their entireties by reference.

TECHNICAL FIELD

The present disclosure relates to biodata verification technology, and more particularly, a biodata verification method for verifying whether an error is in a large amount of biodata received from a client terminal in real time and an apparatus therefor.

BACKGROUND ART

Recently, studies are being intensively made to identify a gene related to a human disease. In particular, rapid progress is made in a project that constructs a gene map by decoding the human genome including genetic information and predicts a human disease through analysis of gene arrangement.

Such a project involves comparing genome data of a particular user to reference genome data, identifying mutated genetic information (i.e., sequencing) of the user, and deducing a correlation with a disease for the user based on identified genetic information.

A service has been introduced for providing a biodata analysis result, in which a particular server receives biodata including sequencing data of a user from a client terminal, analyzes the biodata, and provides an analysis result to the client terminal. That is, it is a service that conducts, by a particular server, a biodata analysis and provides an analysis result to a user. Korean Patent No. 1188886 discloses a system and method for managing genetic information.

However, biodata is a large amount of data. For example, its size is typically about several hundred gigabytes or more. Accordingly, it takes a long time to upload biodata from a client terminal to a server. Also, if a client terminal uploads erroneous biodata to a server, a correct gene analysis is not achieved. In this case, the server must request biodata again to the client terminal and receive the corresponding biodata in response to the request. Furthermore, if the server conducts a gene analysis using erroneous biodata, an error occurs in a result of the gene analysis as well. Moreover, if the server acquires new biodata instead of the erroneous biodata and conducts a gene analysis again using it, resources of the server are unnecessarily consumed and analysis is delayed.

DISCLOSURE

Technical Problem

The present disclosure is designed to solve the problem of the related art, and therefore the present disclosure is directed to providing a method and an apparatus for verifying, in real time, whether an error is in a large amount of biodata received from a client terminal in order to save server resources that may be consumed and an analysis time that may be taken due to erroneous biodata.

These and other objects and advantages of the present disclosure may be understood from the following detailed description and will become more fully apparent from the exemplary embodiments of the present disclosure. Also, it will be easily understood that the objects and advantages of the present disclosure may be realized by the means shown in the appended claims and combinations thereof.

Technical Solution

To achieve the object, a method for verifying biodata according to a first aspect of the present disclosure, which verifies whether an error is in biodata received from a client terminal, includes storing biodata in a storage system, in response to receiving a request for upload of the biodata from the client terminal, extracting each sequence from the biodata and verifying whether the extracted sequence is valid data, calculating an error ratio of the extracted sequences when as a result of the verifying, an erroneous sequence is found, and determining whether the calculated error ratio exceeds a threshold value, and stopping the upload of the biodata when the calculated error ratio exceeds the threshold value.

To achieve the object, an apparatus for verifying biodata according to a second aspect of the present disclosure includes a data processing unit configured to store biodata in a storage system in response to receiving a request for upload of the biodata from a client terminal, a data verification unit configured to extract each sequence from the biodata and verify whether each sequence is valid data, and an error ratio determination unit configured to calculate an error ratio of the sequences based on a number of sequences determined to be erroneous by the data verification unit, and stop the upload of the biodata based on whether the calculated error ratio exceeds a threshold value.

Advantageous Effects

The present disclosure verifies whether an error is in biodata while the biodata is being uploaded, and interrupts the upload of the biodata when an error is found in the biodata and a ratio thereof is greater than a threshold value, thereby preventing an upload phenomenon of inappropriate biodata and save the system resources (storage space and traffic) that may be consumed by analyzing inappropriate biodata.

Also, the present disclosure notifies biodata unsuitable for analysis to a user during upload to induce the user to upload new biodata again, thereby improving satisfaction of a DNA analysis service.

Moreover, the present disclosure stores, in a storage system, an error list in which identification information of a sequence verified to be an erroneous is recorded, to which a reference is made when conducting a biodata analysis, thereby improving efficiency in biodata analysis.

BRIEF DESCRIPTION OF THE DRAWINGS

The accompanying drawings illustrate a preferred embodiment of the present disclosure and together with the foregoing disclosure, serve to provide further understanding of the technical spirit of the present disclosure, and thus, the present disclosure is not construed as being limited to the drawings.

FIG. 3 is a diagram illustrating contents record in decompressed biodata according to an exemplary embodiment of the present disclosure.

MODE FOR CARRYING OUT THE INVENTION

The foregoing objects, features, and advantages will become apparent from the following detailed description with reference to the accompanying drawings, and accordingly, those skilled in the art will be able to easily practice the technical aspects of the present disclosure. Also, in the description of the present disclosure, when it is deemed that certain detailed description of known technology related to the present disclosure may unnecessarily obscure the essence of the disclosure, its detailed description is omitted herein. Hereinafter, an exemplary embodiment of the present disclosure is described in detail with reference to the accompanying drawings.

Unless otherwise defined, it should be understood that the use of the terms "comprises" and/or "comprising", or "includes" and/or "including" when used in this specification, specify the presence of stated elements, but do not preclude the presence or addition of one or more other elements. Also, the term " . . . unit" or "module" as used herein is intended to refer to a processing unit of at least one function or operation, either hardware, a combination of hardware and software, or software.

Figure 1:
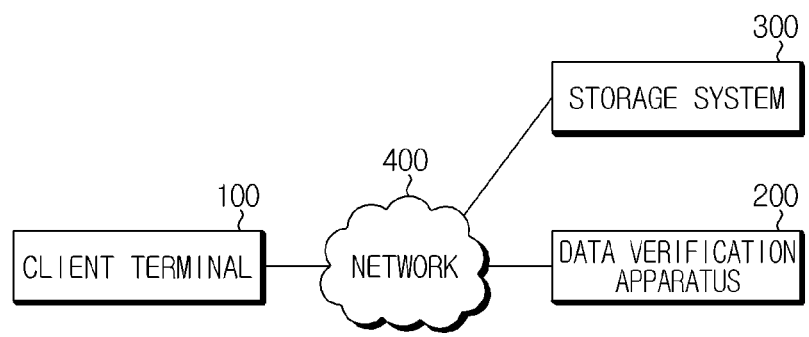
FIG. 1 is a diagram illustrating a biodata verification system according to an exemplary embodiment of the present disclosure.

FIG. 1 is a diagram illustrating a biodata verification system according to an exemplary embodiment of the present disclosure.

As shown in FIG. 1, the biodata verification system according to an exemplary embodiment of the present disclosure includes a client terminal 100, a data verification apparatus 200, and a storage system 300. The client terminal 100, the data verification apparatus 200, and the storage system 300 communicate with each other via a network 400, and the data verification apparatus 200 and the storage system 300 are directly connected to and communicate with each other. Here, the network 400 includes a mobile communication network and a wired Internet network, and in the present disclosure, corresponds to known technology and its detailed description is omitted herein.

The client terminal 100 transmits, to the data verification apparatus 200, biodata having a predetermined format in which sequencing information of a user is recorded. Specifically, the client terminal 100 transmits, to the data verification apparatus 200, compressed biodata in which sequencing information of a particular user is recorded. In this instance, the client terminal 100 may transmit the biodata to the data verification apparatus 200 using a file upload function of hypertext transfer protocol (http) mechanism. The client terminal 100 may produce biodata including several hundred thousand pieces of sequencing information, in conjunction with an analyzer (not shown) that i) analyzes a human genetic material (for example, hairs) of the user, ii) extracts sequencing information from the human genetic material, iii) may compress the produced biodata, and iv) transmit it to the data verification apparatus 200. Alternatively, the client terminal 100 may transmit, to the data verification apparatus 200, compressed biodata which is received from the user and is stored.

The biodata is a file in which the sequencing information of the user is recorded in the form of a text. For example, the biodata has a FASTQ format, consists of several hundred thousand lines, and has a size of 300 gigabytes or more.

The storage system 300 is a system having a storage space in which a large amount of files may be stored. Preferably, the storage system 300 may be a cloud computing system. The storage system 300 stores biodata for each user and stores a gene analysis result obtained by conducting an analysis based on the biodata. Also, the storage system 300 maps an error list to corresponding biodata and stores it. The error list includes identification information of a sequence determined to be erroneous.

When the data verification apparatus 200 receives the compressed biodata from the client terminal 100, the data verification apparatus 200 stores the biodata in the storage system 300, and simultaneously verifies whether the biodata is valid after decompressing the biodata in real time. In this instance, the data verification apparatus 200 continuously extracts a sequence composed of four rows from the decompressed biodata and identifies if there is a valid character and a valid string recorded in each sequence to verify if there is an error in each sequence. When an error ratio of the sequences exceeds a preset threshold value (for example, 5%), the data verification apparatus 200 stops receiving the biodata in progress and notifies the error in the biodata to the client terminal 100.

Figure 2:
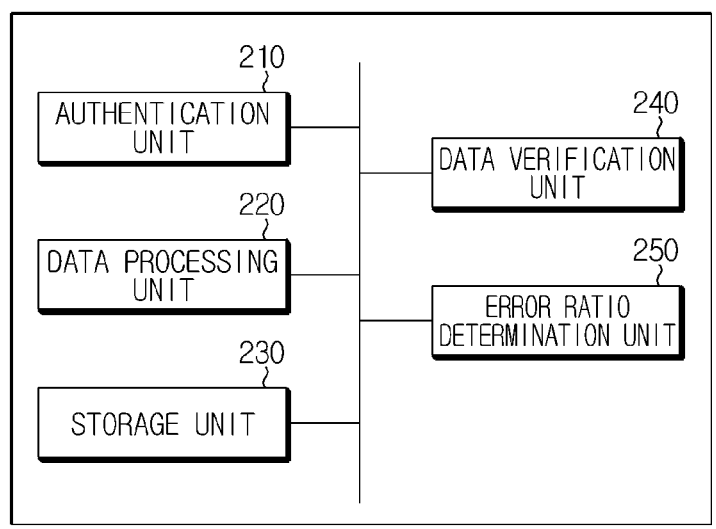
FIG. 2 is a diagram illustrating a biodata verification apparatus according to an exemplary embodiment of the present disclosure.

FIG. 2 is a diagram illustrating a biodata verification apparatus according to an exemplary embodiment of the present disclosure.

As shown in FIG. 2, the data verification apparatus 200 according to an exemplary embodiment of the present disclosure includes an authentication unit 210, a data processing unit 220, a storage unit 230, a data verification unit 240, and an error ratio determination unit 250.

The authentication unit 210 performs a function of authenticating whether the client terminal 100 is a justified user when the client terminal 100 requests for login. In particular, when the authentication unit 210 receives a login request message including identification (ID) and a password from the client terminal 100, the authentication unit 210 identifies whether the ID and the password match with reference based on authentication data stored in the storage unit 230. When authentication succeeds, the authentication unit 210 performs operation for setting a session with the client terminal 100.

The data processing unit 220 performs a function of storing biodata, received from the authenticated client terminal 100, in the storage system 300 and decompressing the biodata. That is, when a large amount of biodata is received from the client terminal 100 within the established session, the data processing unit 220 continuously stores the biodata in the storage system 300 until the receiving of the biodata ends, decompresses the biodata being received in real time, and temporarily stores it in the storage unit 230. In this instance, when biodata is received from the client terminal 100, the data processing unit 220 may identify a compression method based on a file extension name of the biodata and decompress the biodata in real time using the identified compression method. Preferably, the data processing unit 220 stores the biodata in a storage space of the storage system 300 assigned to the user based on the login ID of the user.

When the data processing unit 220 is instructed to delete the biodata from the error ratio determination unit 250, the data processing unit 220 stops receiving the biodata and deletes the biodata that is received from the client terminal 100 and stored from the storage system 300.

FIG. 3 is a diagram illustrating contents recorded in the decompressed biodata according to an exemplary embodiment of the present disclosure.

Referring to FIG. 3, the decompressed biodata records a string in the form of a text. Also, the biodata includes several hundred thousand sequences or more. Each sequence includes four rows. The sequence represents the DNA fragment, and information presented on each row of the sequence is as shown in the following Table 1.

TABLE 1

| Row | Information |
|---|---|
| First row | Sequence ID |
| Second row | Sequencing information |
| Third row | Option |
| Fourth row | Quality score for sequencing |

Referring to Table 1, in the sequence, the first row starts with the character '@', and after the '@', identification information of the sequence is recorded. For example, if '@F5YVAZ0001B1DKT' is recorded in the sequence, identification information of the sequence is 'F5YVAZ0001B1DKT'.

Also, on the second row of the sequence includes sequencing information. As the sequencing information, usually, any one of 'A', 'T', 'G', 'C', and 'N' is recorded. Moreover, the third row of the sequence starts with '+', and various information selected by a provider or a user is recorded after the '+'. For example, on the third row of the sequence, after the '+', sequence identification information may be recorded again or other information may be recorded. On the third row of FIG. 3, after the '+', sequence identification information is found as being recorded again.

Furthermore, on the fourth row of the sequence, a quality score for sequencing is recorded. That is, on the fourth row, quality score measured for each sequencing recorded on the second row is recorded, and each quality score is represented as an American Standard Code for Information Interchange (ASCII) code.

The storage unit 230 stores authentication data including the ID and the password of the user and stores the error list. The error list includes identification information of an erroneous sequence. Also, the storage unit 230 may temporarily store the decompressed biodata.

When the data processing unit 220 decompresses the biodata, the data verification unit 240 continuously extracts a sequence including four rows from the decompressed biodata and determines whether each sequence includes an error.

In particular, the data verification unit 240 i) verifies whether a first row of a sequence starts with '@' and ii) verifies whether there are characters other than 'A', 'T', 'G', 'C', and 'N' defined as a valid character on a second row of the sequence. Further, the data verification unit 240 iii) verifies whether the character '+' is recorded on a third row of the sequence being verified, iv) verifies whether a plurality of characters of a fourth row is a character belonging in a preset ASCII range (for example, ASCII 33 to 126), and v) verifies whether the number of characters in the first row is equal to the number of characters in the fourth row.

When any one of the five verification processes of the sequence fails, the data verification unit 240 records identification information of the corresponding sequence in the error list of the storage unit 230 and reports that an error was found in the sequence to the error ratio determination unit 250. Additionally, the data verification unit 240 extracts each sequence from the decompressed biodata, performs first to fifth verification processes as described above for each sequence. When a sequence having failed any one of the first to fifth verifications is found, the data verification unit 240 reports that an error was found to the error ratio determination unit 250 iteratively as much as the error was found.

When verification of the whole biodata is completed, the data verification unit 240 extracts the error list from the storage unit 230, maps the extracted error list to the biodata, and stores it in the storage system 300.

When biodata is initially received, the error ratio determination unit 250 identifies an overall size of the biodata based on file information recorded in a header of the biodata and estimates the total number of sequences based on the identified overall size of the biodata. Also, when the error ratio determination unit 250 is notified of that an error was found from the data verification unit 240, the error ratio determination unit 250 increases the number of times of finding an error and calculates an error ratio of sequences by dividing the increased number of times finding errors by the estimated total number of sequences. That is, when the error ratio determination unit 250 is notified of that an error was found from the data verification unit 240, the error ratio determination unit 250 calculates an error ratio of sequences based on the estimated total number of sequences and the number of times finding an error.

Moreover, the error ratio determination unit 250 determines whether the calculated sequence error ratio exceeds a preset threshold value (for example, 0.05). When the calculated sequence error ratio does not exceed the preset threshold value, the error ratio determination unit 250 determines that the sequence error occurred is within the range of not influencing biodata analysis and causes biodata to be continuously stored in the storage system 300 through the data processing unit 220. In contrast, when the calculated sequence error ratio exceeds the preset threshold value (for example, 0.05), the error ratio determination unit 250 instructs the data verification unit 240 to interrupt related operations and the verification and the data processing unit 220 to delete the stored biodata. Furthermore, the error ratio determination unit 250 transmits, to the client terminal 100, a message notifying that upload of biodata was stopped due to the occurrence of an error.

Figure 4:
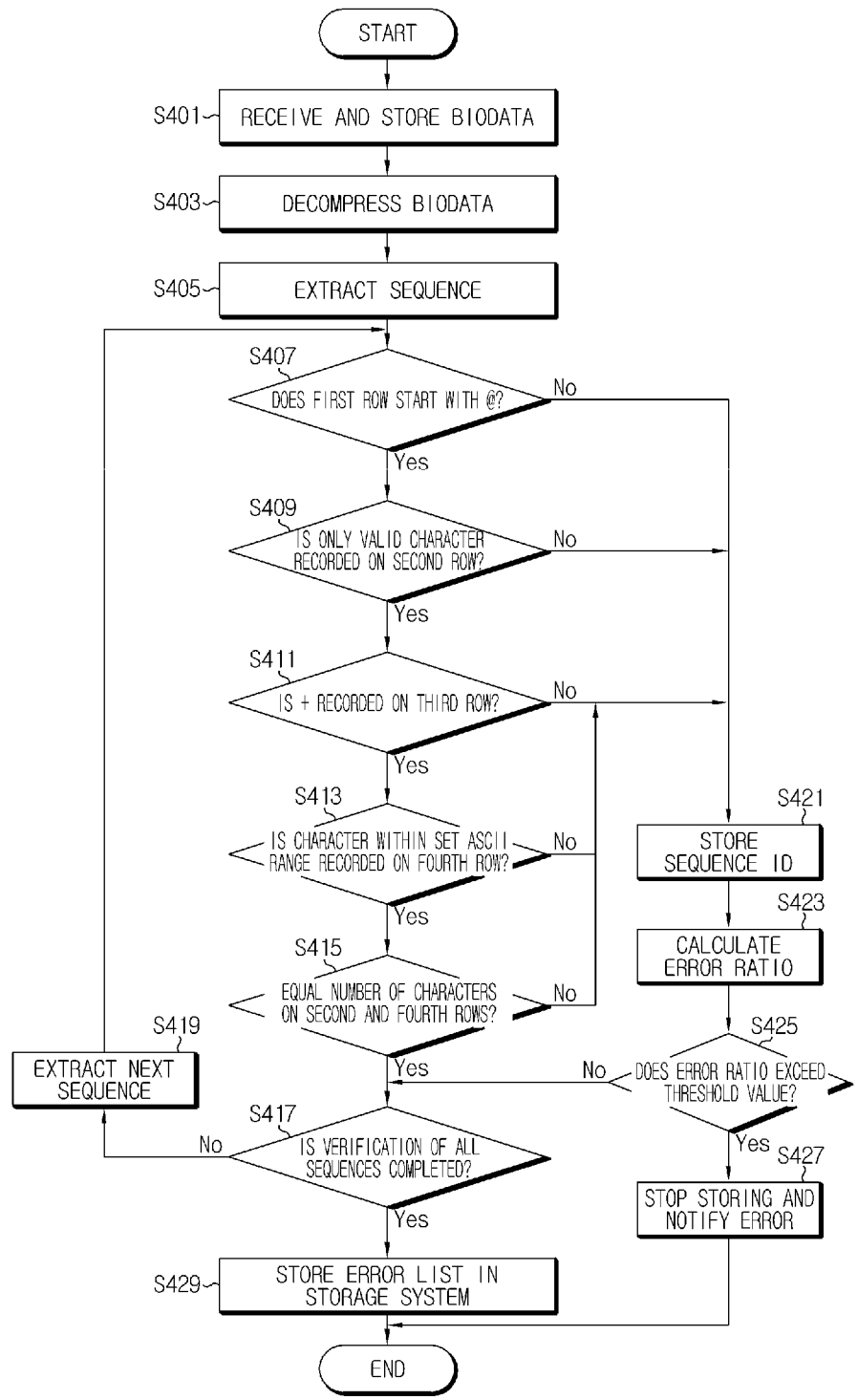
FIG. 4 is a flowchart illustrating a method for verifying biodata received from a client terminal in a biodata verification apparatus according to an exemplary embodiment of the present disclosure.

FIG. 4 is a flowchart illustrating a method for verifying biodata received from the client terminal in the biodata verification apparatus according to an exemplary embodiment of the present disclosure.

Referring to FIG. 4, when the authentication unit 210 receives an access request message including an ID and a password from the client terminal 100, the authentication unit 210 determines whether user information mapped to the ID and the password is recorded in authentication data of the storage unit 230. Subsequently, when authentication of the client terminal 100 succeeds, the authentication unit 210 permits an access of the client terminal 100 and sets a session with the client terminal 100.

Subsequently, the data processing unit 220 receives compressed biodata in a FASTQ format from the authenticated client terminal 100 in real time and stores the received biodata in the storage system 300 (S401). That is, when biodata in a FASTQ format is received from the client terminal 100, the data processing unit 220 accumulates and stores the biodata in the storage system 300 until the receiving of the biodata ends. Preferably, the data processing unit 220 stores the biodata in a storage space of the storage system 300 assigned to the user based on the login ID of the user.

Subsequently, the data processing unit 220 decompresses the compressed biodata received from the client terminal 100 in real time and temporarily stores it in the storage unit 230 (S403). In this instance, when the compressed biodata is received from the client terminal 100, the data processing unit 220 may identify the compression method based on a file extension name of the biodata and decompress the biodata in real time according to the identified compression method.

When the biodata is decompressed by the data processing unit 220, the data verification unit 240 extracts a first sequence from the decompressed biodata (S405). In this instance, the data verification unit 240 extracts first to fourth rows as a first sequence from a text recorded in the decompressed biodata. That is, the data verification unit 240 extracts a first sequence from a plurality of sequences including four rows with an aim of verification.

Subsequently, the data verification unit 240 verifies whether the first row of the extracted first sequence starts with the character '@' (S407). When as a result of the first verification process, the first row of the first sequence starts with the character '@' (i.e., the first verification succeeds), the data verification unit 240 verifies whether characters other than 'A', 'T', 'G', 'C', and 'N' defined as a valid character are recorded on the second row (S409).

Also, when only a valid character is recorded on the second row of the first sequence, the data verification unit 240 determines that the second verification process succeeded and verifies whether '+' is recorded on the third row of the first sequence (S411). Subsequently, when '+' is recorded on the third row, the data verification unit 240 determines that the third verification succeeded and verifies whether a character belonging in a preset ASCII range (for example, ASCII 33 to 126) is recorded on the fourth row (S413). The character recorded on the fourth row represents a quality score of sequencing, and a unique quality score is presented for each character corresponding to a prescribed ASCII range. Additionally, the data verification unit 240 verifies whether characters other than ASCII characters defined by letter grades are recorded on the fourth row.

Subsequently, when all the characters recorded on the fourth row of the first sequence belong in the set ASCII range, the data verification unit 240 determines that the fourth verification succeeded and verifies whether the number of characters recorded on the second row of the first sequence is equal to the number of characters recorded on the fourth row (S415). That is, the data verification unit 240 verifies whether the number of characters on the second row representing sequencing information is equal to the number of characters on the fourth row representing quality scores for each sequencing recorded on the second row. In other words, the data verification unit 240 verifies whether the number of sequencing recorded in the first sequence matches the number of quality scores for the sequencing.

Subsequently, in the first sequence, when the number of characters recorded on the second row is equal to the number of characters recorded on the fourth row, the data verification unit 240 determines that the fifth verification succeeded. Finally, the verification unit 240 determines that the first sequence is a normal sequence.

Subsequently, the data verification unit 240 determines whether verification of all the sequences is completed (S417). That is, the data verification unit 240 determines if there is a sequence not having undergone the verification process among the sequences of the biodata decompressed by the data processing unit 220.

When an unverified sequence is found, the data verification unit 240 extracts a sequence (i.e., a second sequence) next to a verified sequence from the decompressed biodata (S419). That is, the data verification unit 240 extracts, as a sequence to be verified, a sequence consisting of four rows following a verified sequence from the text recorded in the decompressed biodata. Additionally, when verification of the first sequence is completed, the data verification unit 240 extracts a text from fifth to eighth rows as a second sequence to be verified from the text of the decompressed biodata.

Subsequently, the data verification unit 240 performs the process from S407 again to perform the first to fifth verification processes on the second sequence. The data verification unit 240 performs an individual verification for all the sequences by performing S407 to S419, iteratively.

When any one of the first to fifth verification processes fails, the data verification unit 240 stores identification information of a verification failed sequence in an error list of the storage unit 230 (S421). That is, in a sequence being verified, when the first row does not start with '@', when characters other than 'A', 'T', 'G', 'C', and 'N' are recorded on the second row, when '+' are not recorded on the third row, when a particular character recorded on the fourth row does not belong in a set ASCII range, when the number of characters on the second row does not match the number of characters on the fourth row, the data verification unit 240 determines that there is an error in the corresponding sequence and stores identification information of the sequence in an error list of the storage unit 230. In this instance, the data verification unit 240 stores a string following '@' in a sequence determined to be erroneous as identification information of the sequence in the storage unit 230. When a first line of the sequence determined to be erroneous does not start with '@', the data verification unit 240 may regard all characters recorded on the first line of the sequence as identification information of the sequence and store it in the storage unit 230.

Subsequently, after the data verification unit 240 stores the identification information of the sequence in the storage unit 230, the data verification unit 240 reports the occurrence of an error to the error ratio determination unit 250. Then, the error ratio determination unit 250 increases the number of error occurrences by '1', and calculates an error ratio of the sequences by dividing the increased number of error occurrences by a total number of sequences (S423). Preferably, when biodata is initially received through the data processing unit 220, the error ratio determination unit 250 identifies an overall size of the biodata based on file information recorded in a header of the biodata, estimates the total number of sequences for the biodata based on the overall size, and calculates an overall error ratio of the sequences using the estimated total number of sequences. In other words, when the error ratio determination unit 250 is notified of that an error is found from the data verification unit 240, the error ratio determination unit 250 calculates an overall error ratio of the sequences based on the estimated total number of sequences and the number of times finding an error.

After the error ratio determination unit 250 calculates the error ratio of the sequences, the error ratio determination unit 250 determines whether the calculated error ratio exceeds a threshold value (for example, 0.05) (S425). When as a result of the determining, the calculated error ratio of the sequences does not exceed the preset threshold value (for example, 0.05), the error ratio determination unit 250 determines that the sequence error occurred is within the range of not influencing biodata analysis, causes biodata to be continuously stored in the storage system 300 through the data processing unit 220, and continuously verified through the data verification unit 240. That is, although an erroneous sequence is found, when the sequence error ratio so far is less or equal to the threshold value, the data verification apparatus 200 determines that the sequence error occurred is within the range of not influencing biodata analysis, continuously stores the biodata received from the client terminal 100 in the storage system 300, and proceeds with S417 to perform an error verification on other sequence.

In contrast, when the calculated error ratio of the sequences exceeds the preset threshold value (for example, 0.05), the error ratio determination unit 250 determines that source data (i.e., biodata) is too defective to conduct a biodata analysis and instructs the data verification unit 240 to stop verification to stop the sequence verification in progress by the data verification unit 240. Also, the error ratio determination unit 250 instructs the data processing unit 220 to delete the biodata and transmits, to the client terminal 100, a message notifying that upload of biodata was stopped due to the occurrence of an error, to induce the user to upload biodata again (S427). In response to the instructions to delete the biodata as received from the error ratio determination unit 250, the data processing unit 220 stops receiving biodata and deletes the biodata stored so far from the storage system 300.

In S417, when verification of all the sequences is completed, the data verification unit 240 extracts the error list from the storage unit 230, maps the error list to the biodata, and stores it in the storage system 300 (S429).

As described above, the data verification apparatus 200 according to the present disclosure verifies each sequence of biodata received from the client terminal 100 and stops the upload of the biodata when an error ratio of the sequences exceeds a threshold value, thereby saving the system resources (storage space, memory, and traffic) that are consumed when analyzing abnormal biodata. Furthermore, the data verification apparatus 200 according to the present disclosure stores, in the storage system 300, an error list including identification information of an erroneous sequence, to which a reference is made when conducting a biodata analysis, thereby improving operational efficiency in biodata analysis.

While this specification contains many features, the features should not be construed as limitations on the scope of the disclosure or of the appended claims. Certain features described in the context of separate exemplary embodiments can also be implemented in combination in a single exemplary embodiment. Conversely, various features described in the context of a single exemplary embodiment can also be implemented in multiple exemplary embodiments separately or in any suitable subcombination.

Although the drawings describe the operations in a specific order, one should not interpret that the operations are performed in a specific order as shown in the drawings or successively performed in a continuous order, or all the operations are performed to obtain a desired result. Multi-tasking or parallel processing may be advantageous under a particular environment. Also, it should be understood that all exemplary embodiments do not require the distinction of various system components made in the above mentioned embodiment. The program components and systems may be generally implemented as a single software product or multiple software product packages.

The above mentioned method of the present disclosure may be implemented as program instructions and recorded in non-transitory computer-readable media (such as, for example, a compact disk-read only memory (CD ROM), random access memory (RAM), read-only memory (ROM), floppy disks, hard disks, magneto-optical disks, and the like). This process may be easily performed by person having ordinary skill in the technical field to which the present disclosure belongs, and its detailed description is omitted herein.

It should be noted various substitutions, modifications, and changes may be made to the present disclosure by person having ordinary skill in the technical field to which the present disclosure belongs without departing from the spirit and scope of the present disclosure, and the present disclosure is not limited by the above described embodiments and the accompanying drawings.

What is claimed is:

1. A method for verifying biodata received from a client terminal by a data verification apparatus including at least one processor, the method comprising:
    receiving a portion of biodata uploaded through a network from the client terminal and storing the received portion of the biodata in a storage system, wherein the biodata being uploaded by the client terminal includes a plurality of sequences configured according to a specific format, where each of the plurality of sequences includes at least one row;
    extracting at least one sequence from the received portion of the biodata, based on information on a sequence configuration rule of the specific format;
    verifying whether each of the extracted at least one sequence is valid by analyzing information in rows of each of the extracted at least one sequence;
    calculating a sequence error ratio when an erroneous sequence is discovered as a result of the verifying step; and
    suspending an upload of a remaining portion of the biodata when the calculated sequence error ratio exceeds a threshold value,
    wherein the verifying step includes:
        verifying whether rows of a target sequence to be currently verified among the extracted at least one sequence satisfy a row verification condition defined based on the sequence configuration rule of the specific format;
        determining the target sequence as the erroneous sequence when at least one of the rows of the target sequence does not satisfy the row verification condition; and
        determining the target sequence as a valid sequence when the rows of the target sequence satisfy the row verification condition; and
    wherein the calculating step includes:
        calculating a ratio of a number of erroneous sequences to an estimated total number of sequences of the biodata when the target sequence is determined as the erroneous sequence, wherein the erroneous sequences include previously-determined erroneous sequences and the target sequence currently determined as the erroneous sequence.

2. The method according to claim 1, wherein the verifying whether the rows of the target sequence satisfy the row verification condition comprises:
    verifying whether a first row of the target sequence starts with a character '@'; and verifying whether a valid character is recorded on a second row of the target sequence.

3. The method according to claim 2, wherein the verifying whether the rows of the target sequence satisfy the row verification condition further comprises:
   verifying whether a character '+' is recorded on a third row of the target sequence;
   verifying whether a character belonging in a preset American Standard Code for Information Interchange (ASCII) range is recorded on a fourth row of the target sequence; and
   verifying whether a number of characters on the second row is equal to a number of characters on the fourth row.

4. The method according to claim 2, wherein the valid character comprises at least one of 'A', 'T', 'G', 'C', and 'N'.

5. The method according to claim 1, wherein the verifying step comprises:
   when the target sequence is determined as the erroneous sequence, recording identification information of the target sequence in an error list and storing the error list in the storage system.

6. The method according to claim 1, after the suspending step, the method further comprises:
   notifying an occurrence of an error in the biodata to the client terminal; and
   deleting portions of the biodata stored in the storage system.

7. The method according to claim 1, wherein the verifying step comprises:
   decompressing the received portion of the biodata in real time.

8. The method according to claim 1, wherein the calculating step comprises:
   identifying a total amount of the biodata;
   estimating a total number of sequences recorded in the entire biodata based on the total amount; and
   calculating the sequence error ratio by dividing the number of the erroneous sequences with the estimated total number of sequences.

9. The method according to claim 1, wherein the specific format includes a FASTQ format.

10. The method according to claim 8, wherein the total amount of the biodata is identified from file information included in a header of a first received portion of the biodata.

* * * * *